(12) United States Patent
Yao et al.

(10) Patent No.: US 11,034,681 B2
(45) Date of Patent: Jun. 15, 2021

(54) CRYSTAL FORM OF INDOLE DERIVATIVE AND PREPARATION METHOD AND USE THEREOF

(71) Applicant: CHIA TAI TIANQING PHARMACEUTICAL GROUP CO., LTD., Jiangsu (CN)

(72) Inventors: Yuanshan Yao, Shanghai (CN); Bin Chen, Shanghai (CN); Feng Gao, Shanghai (CN); Yuan Chen, Shanghai (CN); Ran Xu, Shanghai (CN); Chengshuai Yang, Shanghai (CN); Sheng Zhang, Shanghai (CN); Jian Li, Shanghai (CN); Shuhui Chen, Shanghai (CN)

(73) Assignee: CHIA TAI TIANQING PHARMACEUTICAL GROUP CO., LTD.

( * ) Notice: Subject to any disclaimer, the term of this patent is extended or adjusted under 35 U.S.C. 154(b) by 0 days.

(21) Appl. No.: 16/963,052

(22) PCT Filed: Jan. 18, 2019

(86) PCT No.: PCT/CN2019/072357
§ 371 (c)(1),
(2) Date: Jul. 17, 2020

(87) PCT Pub. No.: WO2019/141241
PCT Pub. Date: Jul. 25, 2019

(65) Prior Publication Data
US 2020/0347040 A1  Nov. 5, 2020

(30) Foreign Application Priority Data
Jan. 19, 2018  (CN) .......................... 201810052775.1

(51) Int. Cl.
  *C07D 409/06* (2006.01)
(52) U.S. Cl.
  CPC ........ *C07D 409/06* (2013.01); *C07B 2200/13* (2013.01)
(58) Field of Classification Search
  None
  See application file for complete search history.

(56) References Cited

U.S. PATENT DOCUMENTS

| | | | |
|---|---|---|---|
| 2008/0255100 A1 | 10/2008 | Bennani et al. | |
| 2013/0052190 A1* | 2/2013 | Collins et al. | A61K 31/405 424/133.1 |
| 2019/0248770 A1 | 8/2019 | Yao et al. | |

FOREIGN PATENT DOCUMENTS

| CN | 101087784 | 12/2007 |
|---|---|---|
| CN | 107936004 | 4/2018 |
| WO | WO 2005044260 | 5/2005 |
| WO | WO 2005123731 | 5/2006 |
| WO | WO 2018014869 | 1/2018 |

OTHER PUBLICATIONS

International Search Report in International Appln. No. PCT/CN2019/072357, dated Apr. 16, 2019, 6 pages (with English translation).
European Search Report dated May 10, 2021, relating to EP 129757-Sz, 6 pages.
Tumey et al., "3-Idolyl sultams as selective CRTh2 antagonists", Bioorganic & Medicinal Chemistry Letters, 20, 11 (Apr. 14, 2010) 3287-3290, 4 pages.

* cited by examiner

*Primary Examiner* — Brian J Davis
(74) *Attorney, Agent, or Firm* — Fish & Richardson P.C.

(57) ABSTRACT

Disclosed are a crystal form of an indole derivative (compound 1) and a pharmaceutical composition and preparation method thereof. The crystal form is used to prepare a drug for treating a disease related to a CRTH2 receptor.

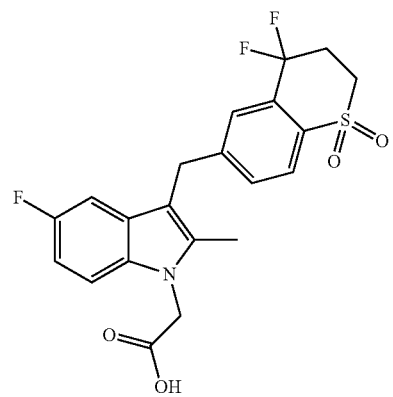

(1)

20 Claims, 2 Drawing Sheets

CRYSTAL FORM OF INDOLE DERIVATIVE AND PREPARATION METHOD AND USE THEREOF

CROSS-REFERENCE TO RELATED APPLICATION

The present application claims the priority and benefit of the Chinese Patent Application No. 201810052775.1 filed at the China National Intellectual Property Administration on Jan. 19, 2018, the disclosure of which is incorporated in its entirety herein by reference.

TECHNICAL FIELD

The present application relates to a crystalline form of an indole derivative and preparation method thereof, and also to the use of the crystalline form in the preparation of a medicament for treating a disease associated with a CRTH2 receptor.

BACKGROUND

CRTH2 (DP2 or GPR44) is a G protein-coupled receptor. After combined with prostaglandin (PGD2), it is involved in the activation and chemotaxis of Th2 lymphocytes, eosinophils and basophils, inhibits the apoptosis of Th2 lymphocytes, and stimulates the production of IL4, IL5 and IL13. These interleukins are involved in important biological responses, including eosinophil recruitment and survival, mucus secretion, airway hyperresponsiveness, and immunoglobulin E (IgE) production.

Ramatroban is a TP (thromboxane-type prostanoid) receptor antagonist, triggering extremely strong vascular and bronchial smooth muscle contraction, and platelet activation. Ramatroban is a weak CRTH2 receptor antagonist. Ramatroban has been approved in Japan for treating allergic rhinitis.

WO2005044260 has reported Compound OC459; and WO2005123731 has reported Compound QAW-039.

Ramatroban

OC459

QAW-039

SUMMARY OF THE INVENTION

In one aspect, the present application provides crystal form A of Compound 1, which has an X-ray powder diffraction pattern with diffraction peaks at the following 2θ angles: 12.78±0.2°, 15.43±0.2°, and 21.25±0.2°, Compound 1

In another aspect, the present application provides a process for preparing the crystal form A of Compound 1, comprising adding Compound 1 to an alcoholic solvent, and recrystallizing or slurrying to obtain the crystal form A.

In another aspect, the present application provides a crystalline composition, wherein the crystal form A of Compound 1 accounts for 50% or more, preferably 80% or more, more preferably 90% or more, and most preferably 95% or more, by weight of the crystalline composition.

In another aspect, the present application provides a pharmaceutical composition, comprising a therapeutically effective amount of the crystal form A of Compound 1 or the crystalline composition as described above.

In a further aspect, the present application provides use of the crystal form A of Compound 1 or the crystalline composition or the pharmaceutical composition as described above for the manufacture of a medicament for treating a disease mediated by a CRTH2 receptor.

In a yet further aspect, the present application provides a method for treating a disease mediated by a CRTH2 receptor, comprising administering to a mammal, preferably a human, in need thereof, a therapeutically effective amount of the crystal form A of Compound 1 or the crystalline composition or the pharmaceutical composition as described above.

In a yet further aspect, the present application provides the crystal form A of Compound 1 or the crystalline composition or the pharmaceutical composition as described above for use in treating a disease mediated by a CRTH2 receptor.

DETAILED DESCRIPTION OF THE INVENTION

In one aspect, the present application provides crystal form A of Compound 1, which has an X-ray powder diffraction pattern with diffraction peaks at the following 2θ angles: 12.78±0.2°, 15.43±0.2°, and 21.25±0.2°, Compound 1

In some embodiments of the present application, the X-ray powder diffraction pattern of the crystal form A of Compound 1 has diffraction peaks at the following 2θ angles: 7.12±0.2°, 12.25±0.2°, 12.78±0.2°, 15.43±0.2°, 18.76±0.2°, 20.02±0.2°, 20.77±0.2°, and 21.25±0.2°.

In some embodiments of the present application, diffraction peaks of the X-ray powder diffraction pattern of the crystal form A of Compound 1 are characterized as follows:

| No. | 2θ Angle (°) | Relative Height (%) |
|---|---|---|
| 1 | 7.12 | 19 |
| 2 | 12.25 | 18 |
| 3 | 12.78 | 44 |
| 4 | 14.05 | 6 |
| 5 | 15.43 | 59 |
| 6 | 16.22 | 12 |
| 7 | 17.34 | 7 |
| 8 | 17.84 | 15 |
| 9 | 18.76 | 31 |
| 10 | 19.65 | 10 |
| 11 | 20.02 | 52 |
| 12 | 20.30 | 8 |
| 13 | 20.77 | 57 |
| 14 | 21.25 | 100 |
| 15 | 21.91 | 6 |
| 16 | 22.15 | 16 |
| 17 | 22.68 | 17 |
| 18 | 23.28 | 7 |
| 19 | 24.14 | 8 |
| 20 | 24.58 | 21 |
| 21 | 24.93 | 9 |
| 22 | 25.37 | 7 |
| 23 | 25.60 | 25 |
| 24 | 26.10 | 17 |
| 25 | 26.75 | 11 |
| 26 | 27.24 | 5 |
| 27 | 27.99 | 12 |
| 28 | 28.46 | 6 |
| 29 | 28.84 | 13 |
| 30 | 29.19 | 5 |
| 31 | 31.07 | 21 |
| 32 | 31.44 | 6 |
| 33 | 32.00 | 6 |
| 34 | 32.69 | 9 |
| 35 | 34.07 | 8 |
| 36 | 34.25 | 8 |
| 37 | 35.57 | 9 |
| 38 | 36.12 | 5 |

Figure 1:
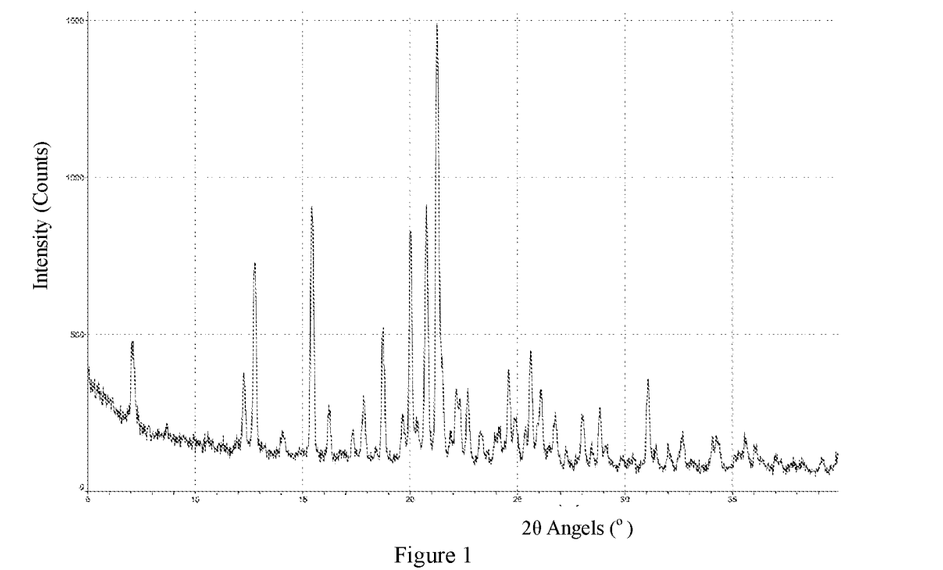
FIG. 1 is an XRPD pattern of the crystal form A of Compound 1.

In some embodiments of the present application, the X-ray powder diffraction pattern of the crystal form A of Compound 1 is substantially as shown in FIG. 1.

The X-ray powder diffraction of the present application uses Cu-Kα radiation. In some embodiments of the present application, the differential scanning calorimetry (DSC) curve of the crystal form A of Compound 1 has an onset of endothermic peak at 278.41° C.±5° C.

Figure 2:
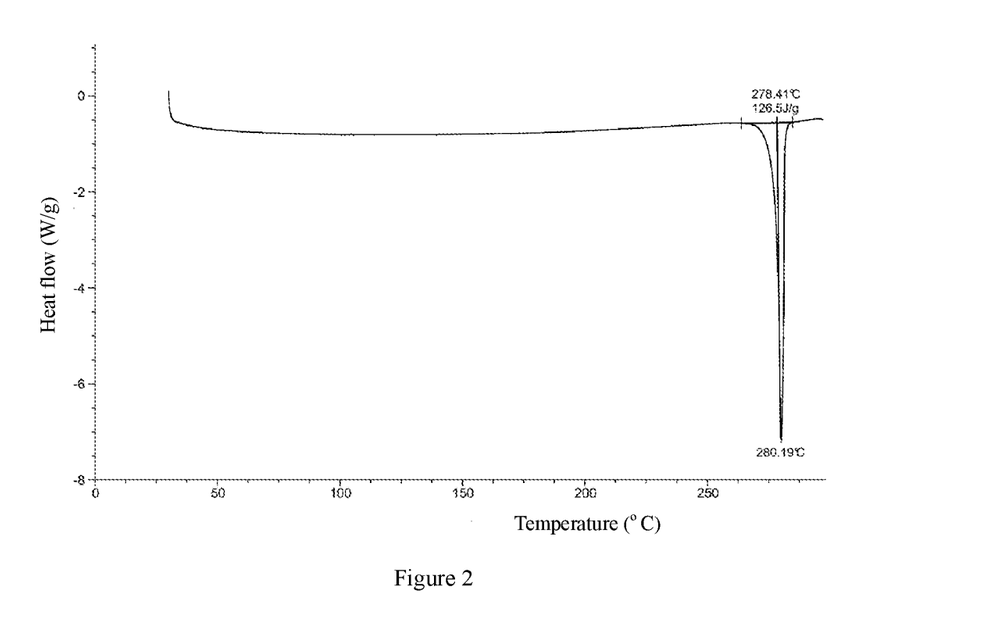
FIG. 2 is a DSC pattern of the crystal form A of Compound 1.

In some embodiments of the present application, the DSC pattern of the crystal form A of Compound 1 is substantially as shown in FIG. 2.

Figure 3:
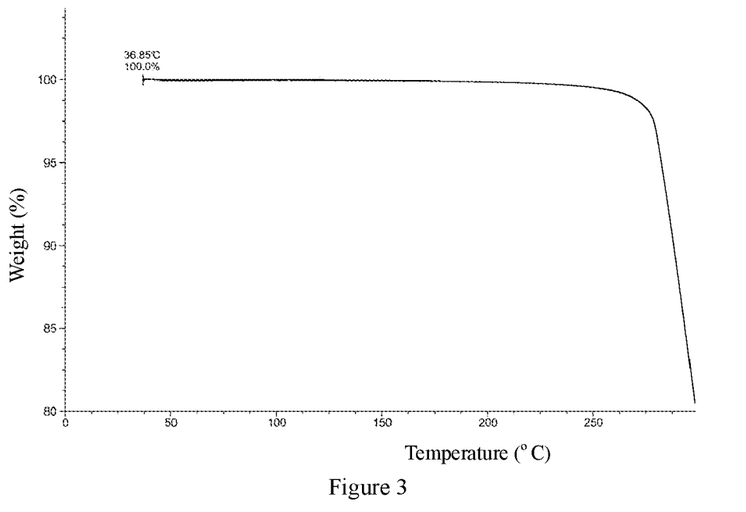
FIG. 3 is a TGA pattern of the crystal form A of Compound 1.

In some embodiments of the present application, the thermogravimetric analysis (TGA) pattern of the crystal form A of Compound 1 is substantially as shown in FIG. 3.

In another aspect, the present application further provides a process for preparing the crystal form A of Compound 1, comprising adding Compound 1 to an alcoholic solvent, and recrystallizing or slurrying to obtain the crystal form A.

In some embodiments of the present application, the alcoholic solvent is selected from one or more of methanol, ethanol, and isopropanol.

In some embodiments of the present application, the alcoholic solvent is ethanol.

In some embodiments of the present application, the process for preparing the crystal form A of Compound 1 further comprising filtering and/or drying.

In some embodiments of the present application, the slurrying temperature in the process for preparing the crystal form A of Compound 1 is 70-90° C. In some embodiments of the present application, the slurrying temperature in the process for preparing the crystal form A of Compound 1 is 80° C.

In another aspect, the present application provides a crystalline composition, wherein the crystal form A of Compound 1 accounts for 50% or more, preferably 80% or more, more preferably 90% or more, and most preferably 95% or more, by weight of the crystalline composition.

In another aspect, the present application provides a pharmaceutical composition, comprising the crystal form A of Compound 1 or the crystalline composition as described above. In some embodiments, the pharmaceutical composition of the present application further comprises a pharmaceutically acceptable adjuvant.

In another aspect, the present application also provides use of the crystal form A of Compound 1 or the crystalline composition or the pharmaceutical composition as described above in the manufacture of a medicament for treating a disease mediated by a CRTH2 receptor.

In another aspect, the present application provides a method for treating a disease mediated by a CRTH2 receptor, comprising administering to a mammal in need thereof a therapeutically effective amount of the crystal form A of Compound 1 or the crystalline composition or the pharmaceutical composition as described above. Preferably, the mammal is a human.

In another aspect, the present application provides the crystal form A of Compound 1 or the crystalline composition or the pharmaceutical composition as described above for use in treating a disease mediated by a CRTH2 receptor.

In some embodiments of the present application, the disease mediated by a CRTH2 receptor is asthma. The crystal form A of Compound 1 of the present application has good stability and is easy to form medicine; its inhibitory effect on a CRTH2 receptor is significant, and in mice model of chronic/acute asthma induced by ovalbumin (OVA) and aluminum hydroxide $(Al(OH)_3)$, the crystal form A of Compound 1 can significantly reduce the number of eosinophils.

Definitions and Description

Unless otherwise indicated, the following terms and phrases as used herein are intended to have the following meanings. A particular term or phrase without a particular definition should not be regarded as being indefinite or unclear, but should be understood in its ordinary sense. When a tradename is used herein, it is intended to refer to the corresponding commodity or its active ingredient.

The term "pharmaceutically acceptable" means those compounds, materials, compositions and/or dosage forms, within the scope of reliable medical judgment, are suitable for use in contact with the tissues of humans and animals without excessive toxicity, irritation, allergic reactions or other problems or complications, while being commensurate with a reasonable benefit/risk ratio.

The term "adjuvant" usually refers to a carrier, diluent and/or medium required for the preparation of an effective pharmaceutical composition.

The "pharmaceutically acceptable carrier" comprises but not limited to any of the following substances approved by the National Drug Administration as acceptable for use in human or livestock animal: adjuvant, excipient, glidant, sweetening agent, diluting agent, preservative, dye/colorant, flavoring agent, surfactant, wetting agent, dispersant, suspending agent, stabilizer, isotonic agent, solvent and/or emulsifier.

The term "treating" or "treatment" means that the compound or formulation of the present application is administrated to prevent, ameliorate or eliminate diseases, or one or more symptoms associated with said diseases, and comprises:

(i) preventing the occurrence of a disease or condition in mammals, particularly when such mammals are susceptible to the condition, but have not yet been diagnosed as suffering from said condition;

(ii) inhibiting a disease or condition, i.e., suppressing the development of the disease or condition;

(iii) alleviating a disease or condition, i.e., causing the regression of the disease or condition.

For a drug or pharmacological active agent, the term "therapeutically effective amount" refers to a sufficient amount of a drug or formulation that can achieve desired effects but is non-toxic. The determination of an effective amount varies from person to person, depending on the age and the general condition of a subject, and also depending on the specific active substance. An appropriate effective amount in individual cases can be determined by the person skilled in the art according to conventional tests.

It should be noted that, in an X-ray diffraction spectrum, a diffraction pattern of a crystalline compound is usually characteristic for a specific crystalline form. Relative intensities of the bands (especially at the low angles) in the diffraction pattern may vary depending upon preferential orientation effects resulting from the differences of crystallization conditions, particle sizes, and other measuring conditions. Therefore, the relative intensities of diffraction peaks are not characteristic for a specific crystalline form. It is the relative positions of peaks rather than relative intensities thereof that should be paid more attention when judging whether a crystalline form is the same as a known crystalline form. In addition, as for any given crystalline form, there may be a slight error in the position of peaks, which is also well known in the field of crystallography. For example, the position of a peak may shift due to the change of a temperature, the movement of a sample or the calibration of an instrument and so on when analyzing the sample, and the measurement error of 2θ value is sometimes about 0.2°. Accordingly, this error should be taken into consideration when identifying a crystal structure. Usually, the position of a peak is expressed in terms of 2θ angle or lattice spacing d in an XRD pattern and the simple conversion relationship therebetween is $d=\lambda/2 \sin\theta$, wherein d represents the lattice spacing, λ represents the wavelength of incident X-ray, and θ represents the diffraction angle. For the same crystalline form of the same compound, the position of peaks in an XRD spectrum thereof has similarity on the whole, and the error of relative intensities may be larger. In addition, it is necessary to point out that due to some factors such as reduced contents, parts of diffraction lines may be absent in the identification of a mixture. At this time, even a band may be characteristic for the given crystalline form without depending upon all the bands of a high purity sample.

It should be noted that DSC is used to measure a transition temperature when a crystal absorbs or releases heat due to the change of the crystal structure or the melting of the crystal. In a continuous analysis of the same crystalline form of the same compound, the error of a thermal transition temperature and a melting point is typically within a range of about ±5° C. When it is said that a compound has a given DSC peak or melting point, it means that the DSC peak or melting point may be varied within a range of ±5° C. DSC provides an auxiliary method to distinguish different crystalline forms. Different crystalline forms can be identified by their characteristically different transition temperatures.

The intermediate compounds of the present application can be prepared through many synthetic methods which are well-known to the person skilled in the art, including the following specific embodiments, embodiments obtained by combining the specific embodiments with other chemical synthetic methods and the equivalent alternative methods which are well-known to the person skilled in the art. The preferred embodiments include but not limited to the examples of the present application.

All the solvents used in the present application are commercially available and can be used without further purification.

The following abbreviations are used in the present application: DMF represents N,N-dimethylformamide; MsOH represents methanesulfonic acid; EtOH represents ethanol; NaOH represents sodium hydroxide.

Vendor directory names are used for the commercially available compounds.

X-Ray Powder Diffraction (X-Ray Powder Diffractometer, XRPD) Method of the Present Application XRPD parameters are as follows:
Light pipe: Cu, Kα, (λ=1.54056 Å).
Voltage of light pipe: 40 kV, Current of light pipe: 40 mA.
Divergence slit: 0.60 mm.
Detector slit: 10.50 mm.

Anti-scatter slit: 7.10 mm.

Scan range: 5 to 40 deg.

Step size: 0.02 deg.

Step length: 0.12 second.

Rotation speed of sample pan: 15 rpm.

Differential Scanning Calorimetry (Differential Scanning Calorimeter, DSC) Method of the Present Application Test method: A sample (0.5 to 1 mg) is taken and placed in a DSC aluminum pan for testing. The sample is heated from room temperature to 300° C. at a heating rate of 10° C./min under the condition of 50 mL/min of $N_2$.

Thermal Gravimetric Analysis (Thermal Gravimetric Analyzer, TGA) Method of the Present Application Test method: A sample (2 to 5 mg) is taken and placed in a TGA platinum pan for testing. The sample is heated from room temperature to 300° C. at a heating rate of 10° C./min under the condition of 25 mL/min of $N_2$.

DETAILED DESCRIPTION OF THE INVENTION

In order to better understand the content of the present application, the present application will be further described in conjunction with the specific examples, but the specific embodiments are not limitations to the content of the present application.

Example 1

-continued

1

Step 1

Compound 1a (10.0 g, 41.13 mmol) was dissolved in methanol (60 mL), and N,N-dimethylformamide (20 mL), triethylamine (20 mL), and [1,1-bis(diphenylphosphino)ferrocene]dichloropalladium (3.01 g, 4.11 mmol) were added. The reaction mixture was stirred under a carbon monoxide atmosphere (50 psi) for 10 hr at 80° C., filtered, concentrated under reduced pressure, then diluted with 100 mL of ethyl acetate and 50 mL of water, and extracted with ethyl acetate (60 mL×2). The organic phases were combined, washed with saturated saline (60 mL×3), dried over anhydrous sodium sulfate, concentrated under reduced pressure to dryness, and purified by silica gel column chromatography (petroleum ether/ethyl acetate=100-0%), to give Compound 1b (7.80 g). $^1$H NMR (400 MHz, CDCl$_3$) δ 8.75 (s, 1H), 8.03-8.00 (dd, J=6.0 Hz, J=8.0 Hz, 1H), 7.37-7.35 (d, J=8.0 Hz, 1H), 3.93 (s, 3H), 3.32-3.28 (m, 2H), 3.04-3.00 (m, 2H).

Step 2

Compound 1b (7.00 g, 31.49 mmol) was slowly added in batch to a solution of bis(2-methoxyethyl)amino in sulfur trifluoride (35 mL). The resulting reaction mixture was stirred for 4 hr at 90° C. After completion of the reaction, the reaction mixture was cooled to room temperature, and diluted with dichloromethane (40 mL). The resulting reaction mixture was slowly added to a saturated aqueous solution of sodium bicarbonate (100 mL) at 0° C. to quench the reaction. The resulting mixture was extracted with dichloromethane (50 mL×2). The organic phases were combined, washed with saturated brine (100 mL×1), dried over anhydrous sodium sulfate, filtered, and concentrated under reduced pressure. The residue was separated and purified by silica gel column chromatography (petroleum ether/ethyl acetate=100-0%), to give Compound 1c (5.80 g). $^1$H NMR (400 MHz, CDCl$_3$) δ 8.38 (s, 1H), 7.94-7.91 (m, 1H), 7.25-7.23 (m, 1H), 3.93 (s, 3H), 3.22-3.19 (m, 2H), 2.65-2.54 (m, 2H).

Step 3

Compound 1c (5.56 g, 22.93 mmol) was dissolved in dichloromethane (60 mL), and m-chloroperoxybenzoic acid (9.31 g, 45.85 mmol, 85%) was added at 0° C. The resulting reaction mixture was stirred for 3 hr at 25° C. After completion of the reaction, the reaction mixture was filtered. A saturated solution of sodium thiosulfate (20 mL) was added to the filtrate to quench the reaction. The organic phase was washed with a saturated aqueous solution of sodium bicarbonate (50 mL), dried over anhydrous sodium sulfate, filtered, and concentrated under reduced pressure. The residue was separated and purified by silica gel column chromatography (petroleum ether/ethyl acetate=100-0%), to give Compound d (4.40 g). $^1$H NMR (400 MHz, CDCl$_3$) δ 8.47 (s, 1H), 8.36-8.34 (m, 1H), 8.05-8.03 (m, 1H), 4.00 (s, 3H), 3.65-3.62 (m, 2H), 3.12-3.06 (m, 2H).

Step 4

Diisobutyl aluminum hydride (1 M, 23.89 mL) was slowly added dropwise to a solution of Compound id (4.4 g, 15.93 mmol) in tetrahydrofuran (50 mL) at 0° C. The reaction mixture was stirred at this temperature for 2 hr. The reaction was quenched by 50 mL of a saturated aqueous solution of potassium sodium tartrate. The resulting mixture was extracted with ethyl acetate (20 mL×2). The organic phases were combined, dried over anhydrous sodium sulfate, filtered, and concentrated under reduced pressure, to give crude Compound 1e. $^1$H NMR (400 MHz, CDCl$_3$) δ 7.95-7.93 (m, 1H), 7.82-7.82 (m, 1H), 7.72-7.70 (m, 1H), 4.85 (s, 2H), 3.61-3.58 (m, 2H), 3.10-3.03 (m, 2H).

Step 5

Compound 1e (4.10 g, 16.52 mmol) was dissolved in dichloromethane (40 mL), and active manganese dioxide (10.05 g, 115.61 mmol) was added. The reaction mixture was stirred for 2 hr at room temperature, and then filtered. The filtrate was directly concentrated. The residue was separated and purified by silica gel column chromatography (petroleum ether/ethyl acetate=100-0%), to give Compound if (3.70 g). $^1$H NMR (400 MHz, CDCl$_3$) δ 10.14 (s, 1H), 8.31 (s, 1H), 8.23-8.21 (m, 1H), 8.15-8.13 (m, 1H), 3.68-3.64 (m, 2H), 3.12-3.06 (m, 2H).

Step 6

Under a nitrogen atmosphere, to a solution of Compound if (3.70 g, 15.02 mmol) and Compound 1g (2.24 g, 15.02 mmol) in 1,2-dichloroethane (50 mL) were added trifluoroacetic acid (5.14 g, 45.05 mmol) and triethylsilane (8.73 g, 75.08 mmol) in sequence. The resulting reaction mixture was stirred for 2 hr at 60° C. After completion of the reaction, 90 mL of a saturated aqueous solution of sodium bicarbonate was added to the reaction mixture, and the resulting mixture was extracted with dichloromethane (30 mL×3). The organic phase was dried over anhydrous sodium sulfate, filtered, and concentrated under reduced pressure, to give crude Compound 1h (5.9 g).

Step 7

Under the protection of nitrogen gas, Compound 1h (5.70 g, 15.02 mmol) was dissolved in N,N-dimethylformamide (80 mL), cesium carbonate (9.79 g, 30.05 mmol) was added, and methyl bromoacetate (2.76 g, 18.03 mmol) was slowly added dropwise under stirring. The reaction mixture was stirred for 2 hr at 25° C., and then poured into water (60 mL), and the resulting mixture was extracted with ethyl acetate (50 mL×2). The organic phase was dried over anhydrous sodium sulfate, filtered, and concentrated under reduced pressure. The crude product was purified by silica gel column chromatography (petroleum ether/ethyl acetate=100-0%), to give Compound 1i (5.1 g).

Step 8

Compound 1i (5.20 g, 11.52 mmol) was dissolved in a mixed solvent of tetrahydrofuran (80 mL) and water (20 mL), and lithium hydroxide monohydrate (1.93 g, 46.07 mmol) was added under nitrogen atmosphere. The reaction mixture was heated to 50° C. and reacted for 1 hr. After completion of the reaction, most of the tetrahydrofuran was distilled off under reduced pressure, and 50 mL of water was added. The resulting mixture was adjusted by addition of 1 mol/L diluted hydrochloric acid to pH 4, and extracted with ethyl acetate (100 mL×3). The organic phase was dried over anhydrous sodium sulfate and filtered. The filtrate was concentrated under reduced pressure. The resulting product was dispersed in 20 mL of ethanol, heated to 80° C. and stirred continuously for 30 min, then cooled to room temperature and filtered. The crude product was separated and purified by preparative high performance liquid chromatography to give Compound 1 (2.75 g). $^1$H NMR (400 MHz, DMSO-d6) δ 13.02 (s, 1H), 7.84-7.82 (m, 1H), 7.71-7.70 (m, 1H), 7.64-7.61 (m, 1H), 7.38-7.37 (m, 1H), 7.22-7.19 (m, 1H), 6.90-6.86 (m, 1H), 4.98 (s, 2H), 4.20 (s, 2H), 3.81-3.78 (m, 2H), 3.02-2.94 (m, 2H), 2.32 (s, 3H). MS-ESI calculated value [M+H]+ 438, measured value 438.

Example 2: Preparation of Crystal Form A

Compound 1 (100.0 g) was slurried in ethanol (400 mL) at 80° C. for 48 hr. The resulting mixture was cooled to room temperature, and filtered with suction to give white solid. The solid was dried in vacuum at 45° C. for 24 hr, to give crystal form A of Compound 1.

The XRPD spectrum of the crystal form A of Compound 1 is shown in FIG. 1. The DSC spectrum of the crystal form A of Compound 1 is shown in FIG. 2. The TGA spectrum of the crystal form A of Compound 1 is shown in FIG. 3.

Experimental Example 1

PathHunter® CHO-K1 CRTH2 β-arrestin cells (DiscoverX, catalogue number 93-0291C2) grew under standard conditions, and were inoculated into a white-wall 384-well microplate at a density of 5,000 cells/well. 20 μL of Cell Plating Reagent 1 was used in each well. Before the test, the cells were incubated overnight at 37° C./5% $CO_2$. A test compound was serially diluted in DMSO with a dilution factor of 3-fold to give 8 concentrations of the test compound. Shortly before the test, the serially diluted test compound was further diluted with the test buffer to 5 times of the test concentration. 5 μL of the further diluted test compound was added to the cells, and the cells were incubated for 30 min at 37° C. The concentration of the solvent was 1%. 5 μL of 6×$EC_{80}$ agonist (PGD2) buffer was added to the cells, and the cells were incubated for 90 min at 37° C. Measured signals were generated by one-time addition of 15 μL (50% v/v) of PathHunter detection mixture reagent and subsequent one-hour incubation. The microplate was read through the chemiluminescent signals of PerkinElmer Envision™ reader. Biological activity of the test compound was analyzed by CBIS data analysis suite (ChemInnovation, CA), and was denoted as $IC_{50}$ value. The experimental results were shown in Table 2.

TABLE 2

| Compound | $IC_{50}$ |
|---|---|
| Compound 1 | <0.1 μM |

Conclusion: Compound 1 has strong antagonistic effect on CRTH2 receptor.

Experimental Example 2

Twelve female C57 BL/6 mice were used in plasma pharmacokinetic assay, randomly divided into two groups, with 6 animals in each group. Animals in the first group were administered intravenously 1 mg/kg of the test drug, and animals in the second group were administered intragastrically 5 mg/kg of the test drug. A formula comprising HPbCD and cosolvent (Solutol®) was used as formulation vehicle, and the obtained intravenous or intragastric formulations were all clear solutions. For animals in the intravenous group and the intragastric group, blood was collected from the saphenous vein at 0.0833, 0.25, 0.5, 1, 2, 4, 8, and 24 hours after administration, with 3 samples at each time point. Plasma samples collected from the intragastric administration group were frozen at −80° C. and thawed before LC-MS/MS sample analysis. The thawed plasma samples were subjected to protein precipitation by adding acetonitrile containing an internal standard in a certain ratio, and centrifuged to obtain a supernatant for LC-MS/MS injection. AP14000 or 5500 was used as the analytical instrument, ACQUITY UPLC BEH C18 (2.1×50 mm, 1.7 μm) was used as the chromatographic column, and the ionization of the test compound was performed by an ESI positive or negative ion source. There were 8 concentrations of the standard sample in each analysis batch, the ratio of the peak area of the test compound to the peak area of the internal standard (IS) was noted as Y, the concentration of the test compound in the plasma sample was noted as X, $1/x^2$ was taken as the weighting coefficient to carry on the linear regression, and the regression equation of response and concentration was obtained. There were also corresponding quality control samples in each analysis batch. Phoenix 6.3 WinNonlin® was used for data processing to give corresponding PK parameters. The experimental results were shown in Table 3.

TABLE 3

|  | Clearance Rate of Intravenous Administration (Cl, mL/min/kg) | Half-life of Intragastric Administration ($T_{1/2}$, hr) | Maximum Blood Concentration of Intragastric Administration ($C_{max}$, nM) | Plasma Exposure of Intragastric Administration (AUC, nM*hr) |
|---|---|---|---|---|
| Crystal Form A of Compound 1 | 4.55 | 3.19 | 6773 | 26015 |

Conclusion: The crystal form A of Compound 1 has good pharmacokinetic properties in mice.

Experimental Example 3

Study on factors influencing the stability of crystal form A of Compound 1 was performed according to the Guiding Principles for Stability Test of Raw Materials and Formulations (9001, Part IV, Chinese Pharmacopoeia, 2015 Edition).

15 mg of the crystal form A of Compound 1 was weighed and placed in the bottom of a glass vial to form a thin layer. Samples placed under high temperature and high humidity conditions were sealed with aluminum foil, and small holes were made in the foil to ensure that the samples can fully contact with ambient air. Samples placed under strong light conditions were sealed with screw caps. The experimental results were shown in the following Tables 4 to 6:

TABLE 4

Results of Solid Stability Test of the Crystal Form A of Compound 1

| Test Condition | Time Point (day) | Crystal Form |
| --- | --- | --- |
|  | 0 | Crystal Form A |
| High Temperature (60° C., Exposure) | 5 | Crystal Form A |
|  | 10 | Crystal Form A |
| High Humidity (Room temperature/ Reletive Humidity 92.5%, Exposure) | 5 | Crystal Form A |
|  | 10 | Crystal Form A |
| Strong Light (5000 1x, Sealed) | 5 | Crystal Form A |
|  | 10 | Crystal Form A |
| 40° C, Reletive Humidity 75%, Exposure | 10 | Crystal Form A |
|  | 30 | Crystal Form A |
|  | 60 | Crystal Form A |
|  | 90 | Crystal Form A |
| 60° C, Reletive Humidity 75%, Exposure | 10 | Crystal Form A |
|  | 30 | Crystal Form A |
|  | 60 | Crystal Form A |
|  | 90 | Crystal Form A |

TABLE 5

| Test Item | 0 Day | 25° C/60% RH | | 30° C/65% RH | |
| --- | --- | --- | --- | --- | --- |
|  |  | 3 months | 6 months | 3 months | 6 months |
| Impurity Content | 0.07% | 0.09% | 0.13% | 0.09% | 0.15% |

TABLE 6

| Test Item | 0 Day | 40° C/75% RH | |
| --- | --- | --- | --- |
|  |  | 1 month | 2 months |
| Impurity Content | 0.07% | 0.17% | 0.13% |

Compound 1

What is claimed is:

1. Crystal form A of Compound 1, wherein an X-ray powder diffraction spectrum of the crystal form A has diffraction peaks at the following 2θ angels: 12.78±0.2°, 15.43±0.2°, and 21.25±0.2°, 2. The crystal form A of Compound 1 according to claim 1, wherein the X-ray powder diffraction spectrum of the crystal form A has diffraction peaks at the following 2θ angels: 7.12±0.2°, 12.25±0.2°, 12.78±0.2°, 15.43±0.2°, 18.76±0.2°, 20.02±0.2°, 20.77±0.2°, and 21.25±0.2°.

3. The crystal form A of Compound 1 according to claim 1, wherein the X-ray powder diffraction spectrum of the crystal form A is substantially as shown in FIG. 1.

4. The crystal form A of Compound 1 according to claim 1, wherein a differential scanning calorimetry curve of the crystal form A has an onset of endothermic peak at 278.41° C.±5° C.

5. The crystal form A of Compound 1 according to claim 4, wherein the differential scanning calorimetry pattern is substantially as shown in FIG. 2.

6. The crystal form A of Compound 1 according to claim 1, wherein a thermogravimetric analysis pattern of the crystal form A is substantially as shown in FIG. 3.

7. A process for preparing the crystal form A of Compound 1 according to claim 1, comprising adding Compound 1 to an alcoholic solvent, and recrystallizing or slurrying to obtain the crystal form A.

8. The process according to claim 7, wherein the alcoholic solvent is selected from one or more of methanol, ethanol, and isopropanol.

9. The process according to claim 8, wherein the alcoholic solvent is ethanol.

10. A crystalline composition, wherein the crystal form A of Compound 1 according to claim 1 accounts for 50% or more, by weight of the crystalline composition.

11. A pharmaceutical composition, comprising the crystal form A of Compound 1 according to claim 1.

12. A method of treating a CRTH2-mediated disease, comprising administering to a mammal in need thereof a therapeutically effective amount of the crystal form A of Compound 1 according to claim 1, wherein the CRTH2-mediated disease is asthma.

13. The crystal form A of Compound 1 according to claim 1, wherein the diffraction peaks of the X-ray powder diffraction pattern of the crystal form A of Compound 1 are characterized as follows:

| No. | 2θ Angle (°) | Relative Height (%) |
| --- | --- | --- |
| 1 | 7.12 | 19 |
| 2 | 12.25 | 18 |
| 3 | 12.78 | 44 |
| 4 | 14.05 | 6 |

-continued

| No. | 2θ Angle (°) | Relative Height (%) |
|---|---|---|
| 5 | 15.43 | 59 |
| 6 | 16.22 | 12 |
| 7 | 17.34 | 7 |
| 8 | 17.84 | 15 |
| 9 | 18.76 | 31 |
| 10 | 19.65 | 10 |
| 11 | 20.02 | 52 |
| 12 | 20.30 | 8 |
| 13 | 20.77 | 57 |
| 14 | 21.25 | 100 |
| 15 | 21.91 | 6 |
| 16 | 22.15 | 16 |
| 17 | 22.68 | 17 |
| 18 | 23.28 | 7 |
| 19 | 24.14 | 8 |
| 20 | 24.58 | 21 |
| 21 | 24.93 | 9 |
| 22 | 25.37 | 7 |
| 23 | 25.60 | 25 |
| 24 | 26.10 | 17 |
| 25 | 26.75 | 11 |
| 26 | 27.24 | 5 |
| 27 | 27.99 | 12 |
| 28 | 28.46 | 6 |
| 29 | 28.84 | 13 |
| 30 | 29.19 | 5 |
| 31 | 31.07 | 21 |
| 32 | 31.44 | 6 |
| 33 | 32.00 | 6 |
| 34 | 32.69 | 9 |
| 35 | 34.07 | 8 |
| 36 | 34.25 | 8 |

-continued

| No. | 2θ Angle (°) | Relative Height (%) |
|---|---|---|
| 37 | 35.57 | 9 |
| 38 | 36.12 | 5. |

14. The process according to claim 7, wherein the slurrying temperature is 70-90° C.

15. A crystalline composition, wherein the crystal form A of Compound 1 according to claim 1 accounts for 80% or more, by weight of the crystalline composition.

16. A crystalline composition, wherein the crystal form A of Compound 1 according to claim 1 accounts for 95% or more, by weight of the crystalline composition.

17. A pharmaceutical composition, comprising the crystalline composition according to claim 10.

18. A method of treating a CRTH2-mediated disease, comprising administering to a mammal in need thereof a therapeutically effective amount of the crystalline composition according to claim 10, wherein the CRTH2-mediated disease is asthma.

19. A method of treating a CRTH2-mediated disease, comprising administering to a mammal in need thereof a therapeutically effective amount of the pharmaceutical composition according to claim 11, wherein the CRTH-2-mediated disease is asthma.

20. A method of treating a CRTH2-mediated disease, comprising administering to a mammal in need thereof a therapeutically effective amount of the pharmaceutical composition according to claim 17, wherein the CRTH-2-mediated disease is asthma.

* * * * *

UNITED STATES PATENT AND TRADEMARK OFFICE
CERTIFICATE OF CORRECTION

PATENT NO. : 11,034,681 B2
APPLICATION NO. : 16/963052
DATED : June 15, 2021
INVENTOR(S) : Yuanshan Yao et al.

It is certified that error appears in the above-identified patent and that said Letters Patent is hereby corrected as shown below:

On the Title Page

Column 1, Line 3, Delete "LTD." and insert -- LTD., Jiangsu (CN) --, therefor.

Column 2, Line 5, Delete "3-Idolyl" and insert -- "3-Indolyl --, therefor.

In the Claims

Column 14, Line 21, In Claim 2, delete "20" and insert -- 2θ --, therefor.

Column 16, Line 25, In Claim 19, delete "CRTH-2-mediated" and insert -- CRTH2-mediated --, therefor.

Column 16, Lines 30-31, In Claim 20, delete "CRTH-2-mediated" and insert -- CRTH2-mediated --, therefor.

Signed and Sealed this
Fourteenth Day of June, 2022

Katherine Kelly Vidal
*Director of the United States Patent and Trademark Office*